US00PP32946P2

(12) United States Plant Patent
Olesen

(10) Patent No.: US PP32,946 P2
(45) Date of Patent: Apr. 6, 2021

(54) COMPACT FLORIBUNDA ROSE PLANT NAMED 'POULPAL085'

(50) Latin Name: *Rosa hybrida*
Varietal Denomination: Poulpal085

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/873,985

(22) Filed: Sep. 3, 2020

(51) Int. Cl.
*A01H 6/74* (2018.01)
*A01H 5/02* (2018.01)

(52) U.S. Cl.
USPC ..... Plt./117

(58) Field of Classification Search
USPC ..... Plt./148
See application file for complete search history.

(56) References Cited

PUBLICATIONS

PLUTO Plant Variety Database Nov. 4, 2020. p. 1.*

* cited by examiner

*Primary Examiner* — Annette H Para

(57) ABSTRACT

A new garden rose plant of the Compact Floribunda class which has abundant, pink apricot blend flowers, strong perfume, and attractive foliage. This new and distinct variety has shown to be uniform and stable in the resulting generations from asexual propagation.

2 Drawing Sheets

Botanical designation: *Rosa hybrida.*
Variety denomination: 'Poulpal085'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poulpal085', originated as a single seedling from the stated cross.

The new variety may be distinguished from its male pollen parent and female seed parent primarily by the following characteristics. The male pollen parent plant has near white flowers while the new variety has pink apricot blend flowers. The female seed parent plant has X flowers while the new variety has pink apricot blend flowers.

The objective of the hybridization of this rose variety was to create a new and distinct variety with unique qualities, such as:

1. Uniform and abundant pink apricot blend flowers with strong perfume;
2. Vigorous, but compact growth when propagated on its own roots;
3. Exceptional disease resistance.

This combination of qualities is not present in previously available commercial cultivars of this type, known to the inventor, and distinguish 'Poulpal085' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poulpal085' was selected in the spring of 2012 by the inventor as a single plant from the progeny of the aforementioned hybridization.

Asexual reproduction of 'Poulpal085' by rooted cuttings was first done by Mogens N. Olesen in the nursery in Fredensborg, Denmark in July, 2012. This initial and other subsequent asexual propagations conducted in controlled environments have demonstrated that the characteristics of 'Poulpal085' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal085'.

Specifically illustrated in FIG. 1 of the drawings are flower petals and sepals detached from the receptacle revealing reproductive flower parts, flower bud, juvenile foliage and stem, mature leaf, and trifoliate leaf.

Figure 1:
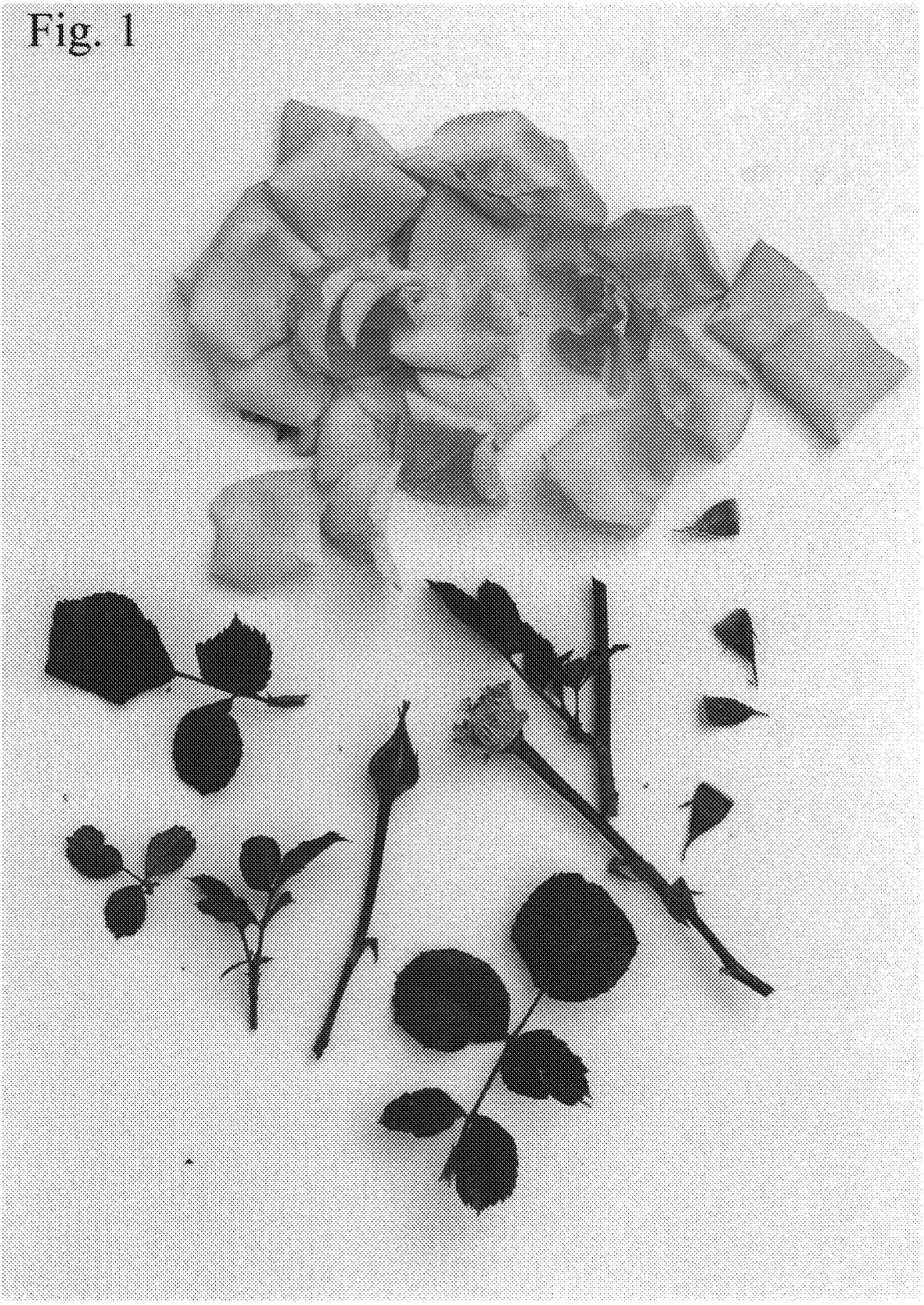
Figure 2:
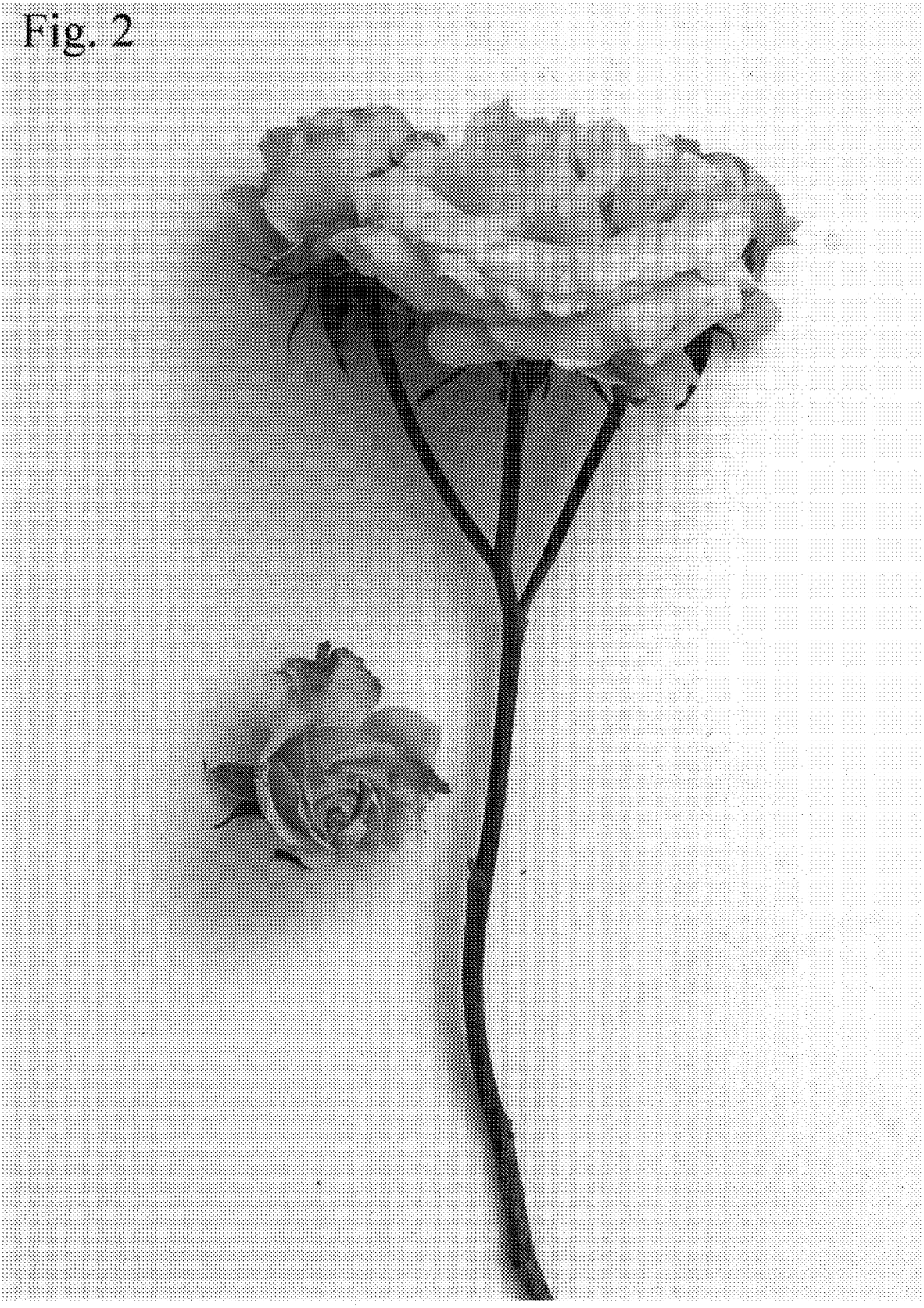

Specifically illustrated in FIG. 2 of the drawings are flower cluster on the branch and above view of flower upon opening. Plants shown are 2 years of age.

DETAILED DESCRIPTION OF THE VARIETY

The following is a description of 'Poulpal085',as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpal062', U.S. Plant Pat. No. 28,168 are compared to 'Poulpal085' in Chart 1.

CHART 1

| | 'Poulpal085' | 'Poulpal062' |
|---|---|---|
| Petal Count | 38 | 50 |
| Flower Diameter | 70 mm | 75 mm |
| General Tonality of Flower Color | Orange Group 28C and Red Group 38A | Red 40C |

FLOWER AND FLOWER BUD

Blooming habit: Continuous.

Flower bud:

*Size.*—Upon opening, 22 mm in length from base of receptacle to end of bud. Bud diameter is 15 mm.

*Bud form.*—Urceolate.

*Sepal inner surface.*—Color: Yellow-Green Group 146D. Surface: Lightly pubescent.

*Sepal outer surface.*—Color: Yellow-Green Group 144A with heavy intonations of Greyed-Orange Group 166B. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—20 mm long, 6 mm wide.

*Receptacle.*—Texture: Smooth. Size: 5 mm in height, 8 mm wide. Color: Yellow-Green Group 144A with intonations of Greyed-Orange Group 166A. Shape: Funnel.

*Pedicel.*—Surface: Smooth. Length: 40 mm. Diameter: 3 mm on average. Color: Yellow-Green Group 144A with strong Greyed-Purple Group 183A. Strength: Strong.

Flower bud development: Flower buds are borne in clusters of about 3 flower buds per stem, or singly.

Flower bloom:

*Fragrance.*—Strong rose perfume.

*Duration.*—The blooms have a duration on the plant of approximately 14 days. Petals fall cleanly away from plant after flowers have fully matured.

*Size.*—Flower diameter is 70 mm when open. Flower depth is 30 mm.

*Flower shape.*—Open cup double flower, with petals that curve out from the center.

*Shape of flower, side view.*—The upper portion is convex. The lower portion is deep concave.

Petalage: Under normal conditions, flowers have about 38 petals.

General tonality of flower: Open flowers are combination of Orange Group 28C and Red Group 38A.

Petal color:

*Upon opening, outer petals.*—Upper surface: Yellow Group 9B at the basal zone, middle zone and outer zone are a blend of Orange Group 29C and Red Group 37B. Lower surface: Orange Group 29C splashed with Orange Group 29A. The apex is Red Group 38C, and basal zone point of attachment is Yellow-Orange Group 18A.

*Upon opening, inner petals.*—Upper surface: Orange Red Group 35A splashed with Yellow Group 13A. Lower surface: Orange Group 29B splashed with Red Group 37A.

*After opening, outer and inner petals are the same color.*—Upper surface: Basal zone spot Yellow Group 12A. Middle and marginal coloration is Red-Purple Group 62B. Lower surface: Red-Purple Group 62C splashed with Red Purple 61D. At the basal zone Yellow Group 13D.

Petals:

*Petal reflex.*—Somewhat reflexed.

*Margin.*—Entire and uniform. Moderate undulations.

*Shape.*—Broad and elliptic. Apex shape: Rounded. Base shape: Acute.

*Size.*—45 mm (l)×47 mm (w).

*Texture.*—Smooth.

*Thickness.*—Average.

Reproductive flower parts:

*Pollen.*—None observed.

*Anthers.*—Size: 2 mm in length. Color: Greyed-Yellow Group 160A. Quantity: 38 on average.

*Filaments.*—Color: Yellow Group 12B. Length: 6 mm.

*Pistils.*—Length: 7 mm. Quantity: 24 on average.

*Stigmas.*—Color: Yellow Group 3D.

*Styles.*—Color: Green-White Group 157A.

*Location of stigmas.*—Even in location relative to the length of the filaments and the height of the anthers.

*Hips.*—None Observed.

PLANT

Plant growth: Upright, very compact, and well branched. Plants are 40 cm in height, and 38 cm wide.

Stems:

*Color of juvenile growth.*—Yellow-Green Group 144B.

*Color of mature growth.*—Yellow-Green Group 144A.

*Length.*—Canes are about 18 cm from the base of the plant to the flowering portion.

*Diameter.*—About 6 mm.

*Internodes.*—On mature canes about 40 mm between nodes.

*Surface texture.*—Young wood: Smooth. Older wood: Smooth.

Long prickles: None observed.

Plant foliage:

Compound leaf: 95 mm (1) x 70 (w).

*Quantity.*—2 leaves per 10 cm of stem on average.

*Leaf bearing angle to the stem.*—45 degrees.

*Color of juvenile foliage.*—Upper side: Yellow-Green Group 144A with strong intonations of Greyed-Purple Group 183A. Lower side: Yellow-Green Group 144A with strong intonations of Greyed-Purple Group 183A.

*Color of mature foliage.*—Upper side: Yellow-Green Group 147A. Lower side: Yellow-Green Group 146B.

Plant leaves and leaflets:

*Stipules.*—Size: 6 mm long, 2 to3 mm wide. Quantity: 2 per compound leaf. Shape: Linear, slightly broad based with outward extending apices. Margins: Finely serrated. Color: Yellow-Green Group 144B.

*Petiole.*—Length: 16 mm. Diameter: 2 mm. Upper surface color: Yellow-Green Group 144A, with other intonations of Greyed-Purple Group 183B. Lower surface color: Yellow-Green Group 144A.

*Rachis*.—Length: About 40 mm. Upper surface color: Yellow-Green Group 144A, with other intonations of Greyed-Purple Group 183B. Lower surface color: Yellow-Green Group 144A.

*Leaflet*.—Quantity: Normally 5 leaflets. Margins: Serrated. Size: 35 mm long, and 35 mm wide. Shape: Generally elliptical. Base: Rounded. Apex: Rounded, and mucronate. Texture: Smooth. Thickness: Average. Arrangement: Odd pinnate. Venation: Reticulate. Glossiness: Very glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Compact Floribunda rose class named 'Poulpal085', substantially as illustrated and described herein, due to its abundant pink apricot blend flowers, strong perfume, disease resistance, and extended period of bloom.

* * * * *